Figure 1:
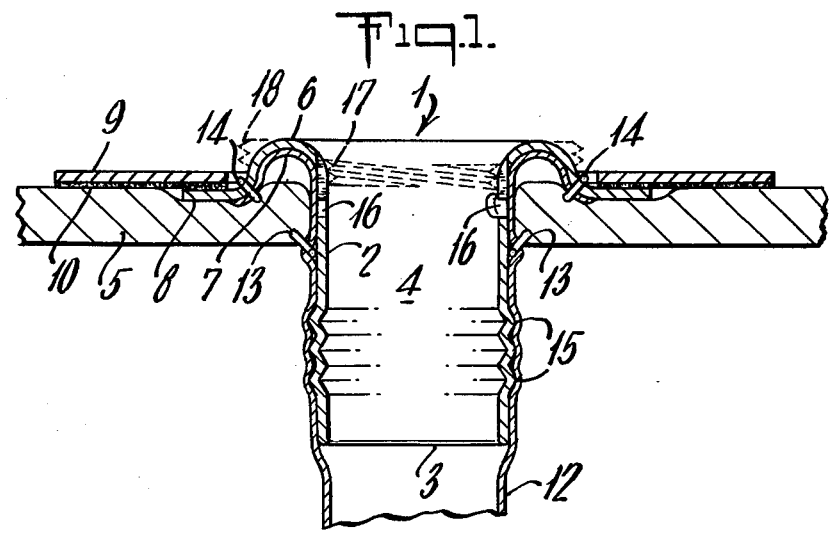

United States Patent [19]

Hill

[11] 4,265,244
[45] May 5, 1981

[54] STOMA ADAPTOR

[75] Inventor: Roger C. Hill, Skipton, England

[73] Assignee: Johnson & Johnson, New Brunswick, N.J.

[21] Appl. No.: 10,275

[22] Filed: Feb. 7, 1979

[51] Int. Cl.³ .............................................. A61F 5/44
[52] U.S. Cl. ........................................... 128/283; 3/1
[58] Field of Search ................... 128/283, 334 C; 3/1, 3/1.1

[56] References Cited

U.S. PATENT DOCUMENTS

| 2,564,399 | 8/1951 | Franken | 128/1 R |
|---|---|---|---|
| 2,931,353 | 4/1960 | Kitzul | 128/1 R |
| 3,216,420 | 11/1975 | Smith et al. | 128/283 |
| 3,254,651 | 6/1966 | Collito | 128/334 C |
| 3,447,533 | 6/1969 | Spicer | 128/283 |
| 3,815,577 | 6/1974 | Bucalo | 128/1 R |
| 4,121,589 | 10/1978 | McDonnell | 128/283 |
| 4,183,357 | 1/1980 | Bentley et al. | 3/1 |

FOREIGN PATENT DOCUMENTS

| 2634642 | 2/1977 | Fed. Rep. of Germany . |
| 2558521 | 6/1977 | Fed. Rep. of Germany . |
| 2648222 | 4/1978 | Fed. Rep. of Germany . |

Primary Examiner—Robert W. Michell
Assistant Examiner—T. J. Wallen
Attorney, Agent, or Firm—Irving Newman

[57] ABSTRACT

A stoma adaptor comprising an open tube of non-toxic material, having a proximal end for insertion into the lumen of a body orifice at a stoma site; a distal end at which the rim is turned outwards to form an annular lip having a concave underside geometrically continuous with the rest of the tube whereby an open live intestine advanced over the tube from the proximal end will take up a similarly flared configuration for attachment to the external periphery of the orifice; means for securing an open intestine to the outer surface of the tube; means for securing the tube to the body wall; and means for attachment to the tube, at the distal end thereof, of a fluid-tight stoma closure.

7 Claims, 2 Drawing Figures

U.S. Patent May 5, 1981 4,265,244

STOMA ADAPTOR

The invention relates to an accessory or fitting for a body orifice, by which we mean an external opening in an internal passage of a living body and which we refer to for convenience as a stoma. The accessory or fitting takes the form of an adaptor which may be permanent, for use in facilitating closure of, or attachment of other fittings to, the stoma.

The invention is applicable by way of example in a stoma such as an artificial anus or colostomy, or an ileostomy, but is also contemplated for any other such body orifice which is liable to produce an exudate or effluent which needs to be controlled or collected.

Devices for sealing an artificial anus have previously been proposed which have a flexible closure plug for introduction into the lumen of the intestine, and an abutment portion for laying on the outside of the body, generally the abdominal wall of the user. For the most part such prior devices are technically complicated and particularly prone to contamination, and difficulty is experienced both in preventing their involuntary release and, in a mechanical sense, in their use by the elderly, who are the principal users of an artificial anus in cases of cancer of the large intestine. Adequate sealing cannot be accomplished with these previously proposed devices. Moreover, they are generally not disposable, so that the cleansing required is nauseating.

In practice therefore tightly fitting closures or plastic bags that are attachable by adhesion continue to be used. These two arrangements have considerable disadvantages. The known closures have to be pressed on by means of a girdle under fairly substantial pressure in order to seal the artificial anus. Apart from the fact that the wearing of such closures is consequently unpleasant, the use of such closures tends to distort the intestinal tissues and to cause haemorrhages and inflammation. During movements of the body, the closure may moreover become displaced from the artificial anus, so that the latter is frequently exposed. The adhesively attachable plastic bags, on the other hand, are intended and suitable only for collecting, but not for holding back, excreta and intestinal gases. Since a person equipped with an artificial anus lacks the facility to hold back excreta and intestinal gases voluntarily and the discharge of excreta and intestinal gases into the plastic bag causes considerably acoustically apprehensible noise and a characteristic smell during bowel movement, the user is considerably handicapped socially when when such plastic bags are used properly. The adhesively attached bags moreover have the disadvantage that the weight of the more or less filled plastic bag causes discomfort and may result in the bag becoming involuntarily detached from the user's skin, particularly in summer when the skin perspires. Here also the wearing of a girdle is recommended.

Devices have recently been proposed for stoma closures without the foregoing disadvantages. British Pat. No. 31230/74 describes a device comprising a flexible absorbent disposable closure plug for introduction into the lumen, and a disc-shaped flexible abutment portion bearing an annular region of adhesive on one side for placement against the user's abdominal wall adjacent the stoma to hold the device in place while sealing against escape of fluids. A helical pin is secured to and projects from the same side of the abutment portion and the closure plug is pushed or twisted onto the pin and thereby locked in place.

In our British Pat. No. 37534/77, corresponding to U.S. Patent Application Ser. No. 939,149, filed Aug. 30, 1978, we propose as an abutment for a stoma, a flexible adhesive sheet adapted to retain an absorbent flexible closure plug such as a tampon within the lumen of the stoma passage by means embracing the distal end of the plug. The attachment of the plug to the abutment may be permanent or temporary and in the latter case the plug may be replaceable without detaching the abutment from the stoma opening. The connection between plug and abutment may for example be a bayonet fitting, a press fit or snap fit, a clamp, or other locking device. In general the plug is fitted in the passage by insertion through an opening in the adhesive sheet corresponding to the opening in the body.

Such devices covering an artificial anus may be provided with a permeable section incorporating a filter made, for example, of charcoal, to allow the passage of flatus while reducing or eliminating odor. Such a device may be used with the present invention.

When an artificial orifice such as an artificial anus is constructed, a hole is made in the patient's abdominal wall, and, after separation from the rectum, the open end of the intestine is passed through the hole and held in place by two rows of sutures, a first row on the inner periphery of the hole in the abdominal wall and a second row round the outside of the hole, where the open end of the intestine has been expanded and turned slightly back on itself over the edge of the hole.

The size and shape of the opening is very much a matter of the surgeon's skill, and, as is well known in the art of stoma care, much variation is found between individual stomata.

It is an object of the invention to provide a stoma adaptor, having one of a range of standard sizes, which can be permanently incorporated in the stoma to facilitate the fitting of an accessory such as a closure plug, a bag or other receptacle, or other ancillary equipment.

It is a further object of the invention to provide such an adaptor enabling stoma accessories to be used and replaced with minimal or no repeated removal of adhesive from the wearer's skin and without having to remove the adaptor itself. Frequent changing of adhesive appliances is a major cause of discomfort in stoma patients.

It is a still further object to provide a stoma adaptor which is hygienic, and ensures optimum conditions of cleanliness and simple operation together with comfortable use and reliable sealing.

According to the present invention we provide a stoma adaptor comprising: an open tube of non-toxic material, having a proximal end for insertion into the lumen of a body orifice at a stoma site; a distal end at which the rim is turned outwards to form an annular lip having a concave underside geometrically continuous with the rest of the tube whereby an open live intestine advanced over the tube from the proximal end will take up a similarly flared configuration for attachment to the external periphery of the orifice; means for securing an open intestine to the outer surface of the tube; means for securing the tube to the body wall; and means for attachment to the tube at the distal end thereof, of a fluid-tight stoma closure.

The external diameter of the open tube, which is generally cylindrical, should be such that the open end of the intestine may be slid over it from the proximal end like a sock. The intestine is to be advanced along the tube and to follow the outer surface of the lip, without encountering hindrances such as corners, outwardly and round and flared to form a lip on the rim of the intestine which can be held between the lip of the adaptor and the periphery of the hold in the abdominal wall.

Figure 2:
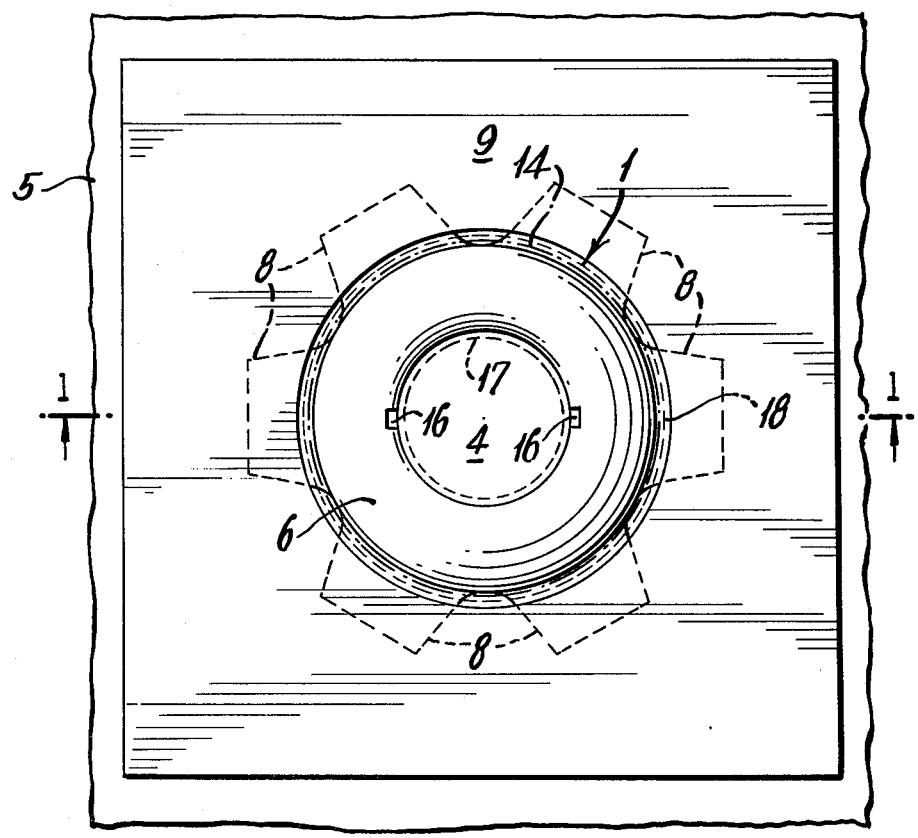

The invention is illustrated by the accompanying drawing in which:

FIG. 1 shows an adaptor of the invention in longitudinal cross-section fitted in an abdominal wall; and FIG. 2 shows an exterior plan view of the adaptor.

Referring to the Figures, there is shown an adaptor 1 comprising an open tube 2 having a proximal end 3 inserted into an orifice 4 in the abdominal wall 5 of a patient. The distal end of the tube 2 opens out to form a circular lip 6 having a concave annular underside 7 continuous with the tube, that is without any corners. The outer edge of the lip 6 is formed with integral tabs 8 which lie flush with the abdominal wall. An adhesive sheet 9 with the adhesive layer 10 lowermost and having a central hole 11 exposing the adaptor lip, adheres to the skin of the wall 5 and holds the tabs 8 firmly against the wall, thus helping to secure the adaptor in place, and protecting the skin surrounding the orifice from the effect of exudate. Since in this application the adhesive material will be in constant contact with the skin, the adhesive should be one which has minimal irritant effect on the skin.

Before or after the intestine is secured to the abdominal wall by a row of sutures 13, the open intestine 12 is slid over the proximal end 3 of the tube 2 and follows the curved underside 7 of the lip 6 so as to lie under the outer edge of the lip but over the abdominal wall 5, the adaptor being brought flush with the wall. Suture rows at 14 are then made to secure the adaptor and the intestine to the abdominal wall; sutures 14 pass through small holes in the outer edge of the lip 6. The intestine is restrained from sliding off the tube by virtue of ribs 15, in the tube surface, which may also serve to assist in the fitting and retention of a closure plug. Alternatively or additionally the intestine may be held in place on the tube by means of surgical tissue adhesive on the outer surface of the tube at 15.

For the attachment of normally internal fittings such as closure plugs, the mouth of the adaptor is formed with grooves or slots 16 to cooperate with pins on the fitting in forming a bayonet lock, and/or with an internal screw thread 17. For the attachment of receptacles such as collector bags used in the art an external screw thread 18 is provided. The screw threads may or may not be tapered, and a milled edge or other device may be provided on the adaptor, to facilitate screwing operations. Standard attachments are made possible by the standardisation of the adaptor, and are attached without the use of adhesives other than on the semi-permanent sheet 9. Bayonet grooves or slots may be provided also on the exterior of the adaptor mouth and other variations and methods of attachment are within the scope of the invention. It will be appreciated that the adaptor may, but need not, possess more than one means for securing an attachment and is shown here with more than one for the sake of illustration.

The open tube may be made of any suitably film material, such as a synthetic resin or metal compatible with, or rendered compatible, e.g. by coating, with the tissue, or may be a composite construction. The adhesive sheet may be any of the types well known in the art.

The term "stoma closure" is to be understood in a broad sense to include not only such elements as plugs but also receptacles such as bags which effectively terminate the channel for exudate by collecting it. Moreover it will be appreciated that the means for attachment of a stoma closure can be adopted for attachment of other elements such as equipment required to communicate with the lumen of the stoma.

What I claim is:

1. A stoma adaptor comprising: an open tube of nontoxic material, having a proximal end for insertion into the lumen of a body orifice at a stoma site and a distal end, said distal end comprising a rim turned outwards to form an annular lip having a concave underside geometrically continuous with the rest of the tube, whereby an open live intestine advanced over the tube from the proximal end will take up a similarly flared configuration for attachment to the external periphery of the orifice; means for securing an open intestine to the outer surface of the tube; means for securing the tube to the body wall, said means for securing the tube to the body wall comprising tabs formed integral with the outer edge of said annular lip for underlying an adhesive sheet placed on the skin around the stoma, and further including holes in said annular lip adapted for suturing therethrough; and means for attachment to the tube, at the distal end thereof, of a fluid-tight stoma closure.

2. An adaptor according to claim 1, wherein the open tube is cylindrical apart from the rim at the distal end.

3. An adaptor according to claim 2, wherein the tube is made of plastic material.

4. An adaptor according to claim 2, wherein said means for securing the intestine comprises a circumferential ribbed configuration on the tube.

5. An adaptor according to claim 1 wherein said stoma closure attachment means comprises grooves, slots or screw threads formed at the mouth of the tube to cooperate with fastening means on an accessory.

6. An adaptor according to claim 1 in operative association with a fitted closure plug or bag.

7. A plurality of adaptors as claimed in claim 1, in a range of different sizes.

* * * * *